US012674802B2

(12) United States Patent
Torsi et al.

(10) Patent No.: US 12,674,802 B2
(45) Date of Patent: Jul. 7, 2026

(54) METHOD OF FUNCTIONALIZATION OF A GATE ELECTRODE OF A FIELD-EFFECT TRANSISTOR SENSOR

(71) Applicant: UNIVERSITA' DEGLI STUDI DI BARI ALDO MORO, Bari (IT)

(72) Inventors: Luisa Torsi, Bari (IT); Gerardo Palazzo, Bari (IT); Gaetano Scamarcio, Bari (IT)

(73) Assignee: UNIVERSITA' DEGLI STUDI DI BARI ALDO MORO, Bari (IT)

( * ) Notice: Subject to any disclaimer, the term of this patent is extended or adjusted under 35 U.S.C. 154(b) by 731 days.

(21) Appl. No.: 16/474,707

(22) PCT Filed: Dec. 18, 2017

(86) PCT No.: PCT/IB2017/058065
§ 371 (c)(1),
(2) Date: Jun. 28, 2019

(87) PCT Pub. No.: WO2018/122671
PCT Pub. Date: Jul. 5, 2018

(65) Prior Publication Data
US 2019/0331673 A1     Oct. 31, 2019

(30) Foreign Application Priority Data

Dec. 30, 2016 (EP) .................................... 16207596

(51) Int. Cl.
*G01N 33/543* (2006.01)
*G01N 27/414* (2006.01)
(Continued)

(52) U.S. Cl.
CPC ..... *G01N 33/5438* (2013.01); *G01N 27/4145* (2013.01); *G01N 33/54393* (2013.01);
(Continued)

(58) Field of Classification Search
CPC ........... G01N 33/5438; G01N 27/4145; G01N 33/54393; G01N 33/6854; G01N 2610/00; G01N 33/551
(Continued)

(56) References Cited

U.S. PATENT DOCUMENTS

| | | | | |
|---|---|---|---|---|
| 5,063,081 | A * | 11/1991 | Cozzette | G01N 35/0099 435/7.1 |
| 2001/0014461 | A1* | 8/2001 | Hutchens | C12Q 1/00 435/7.92 |

(Continued)

OTHER PUBLICATIONS

Hideshima et al., Detection of tumor marker in blood serum using antibody-modified field effect transistor with optimized BSA blocking, Sensors and Actuators B: Chemical, vol. 161, pp. 146-150. (Year: 2012).*

(Continued)

*Primary Examiner* — Christopher L Chin
(74) *Attorney, Agent, or Firm* — Victor Cardona, Esq; Heslin Rothenberg Farley & Mesiti P.C.

(57) ABSTRACT

A method of functionalization of a gate electrode of a field-effect transistor sensor includes forming a layer of biological recognition elements on a surface of said gate electrode, wherein said layer of biological recognition elements includes a self-assembled structure of one or more specific-binding-pair-forming substances (anti-hIg, anti-IgG, anti-IgM). The layer of biological recognition elements is treated with a solution containing a blocking agent to fill vacancies and prevent nonspecific binding in the self-assembled structure. One or more specific-binding-pair-forming substances immobilized in said layer of biological recognition elements are packed at a density of $0.1 \times 10^4$ $\mu m^{-2}$ and $10 \times 10^4$ $\mu m^{-2}$, preferably between $1 \times 10^4$ $\mu m^{-2}$ and $2 \times 10^4$ $\mu m^{-2}$.

9 Claims, 11 Drawing Sheets

(51) Int. Cl.
G01N 33/551 (2006.01)
G01N 33/68 (2006.01)

(52) U.S. Cl.
CPC ....... G01N 33/551 (2013.01); G01N 33/6854 (2013.01); G01N 2610/00 (2013.01)

(58) Field of Classification Search
USPC ........................ 436/524, 809, 525, 151, 806; 204/403.01, 290.01; 422/82.01, 82.02; 435/962
See application file for complete search history.

(56) References Cited

U.S. PATENT DOCUMENTS

2003/0102510 A1* 6/2003 Lim ...................... B82Y 15/00 257/368
2014/0061728 A1* 3/2014 Trivedi ................ G01N 27/414 257/253

OTHER PUBLICATIONS

Briand et al., Functionalisation of gold surfaces with thiolate SAMs: Topography/bioactivity relationship—A combined FT-RAIRS, AFM and QCM investigation, ScienceDirect, vol. 601, pp. 3850-3855. (Year: 2007).*

Lu et al., ("CMOS—Compatible Silicon Nanowire Field-Effect Transistors for Ultrasensitive and Label-Free MicroRNAs Sensing" Small No. 10, 2022-2028 (2014)) (Year: 2014).*

International Search Report and Written Opinion of the International Searching Authority for PCT/IB2017/058065 mailed on Feb. 23, 2018.

Cheng, S., et al., "Field Effect Transistor Biosensor Using Antigen Binding Fragment for Detecting Tumor Marker in Human Serum", Materials, vol. 7, No. 4, pp. 2490-2500 (2014).

Mulla, M.Y., et al., "Capacitance-modulated transistor detects odorant binding protein chiral interactions", Nature Communications, vol. 6, pp. 1-9 (2015).

Torsi, L., et al., "Oragnic field-effect transistor sensors: a tutorial review", Chemical Society Reviews, vol. 42, pp. 8612-8628 (2013).

Cramer, T., et al., "Water-gated organic field effect transistor—opportunities for biochemical sensing and extracellular signal transduction", Journal of Materials Chemistry B, vol. 1, pp. 3726-3741 (2013).

Magliulo, M., et al., "Label-free C-reactive protein electronic detection with an electrolyte-gated organic field-effect transistor-based immunosensor", Analytical and Bioanalytical Chemistry, vol. 408, pp. 3943-3952 (2016).

Shen, Z., "Label-Free Biomolecular Sensors Using Recombinant Antibody, Carbohydrate, or DNA", Retrieved from the Internet: URL:http://media.proquest.com/media/pq/classic/doc/1610730111/fmt/ai/rep/SPDF?cit:auth=Shen,+Zhihong&cit:title=Label+-free+biomolecular+sensor+using+recombinant+antibody,+carbohydrate,+or+DNA&cit:pub=ProQuest+Dissertations+and+Theses&cit:vol=&cit:iss=&cit:pg=&cit:date=2008&ic=true&cit:prod=ProQuest+Dis.

* cited by examiner

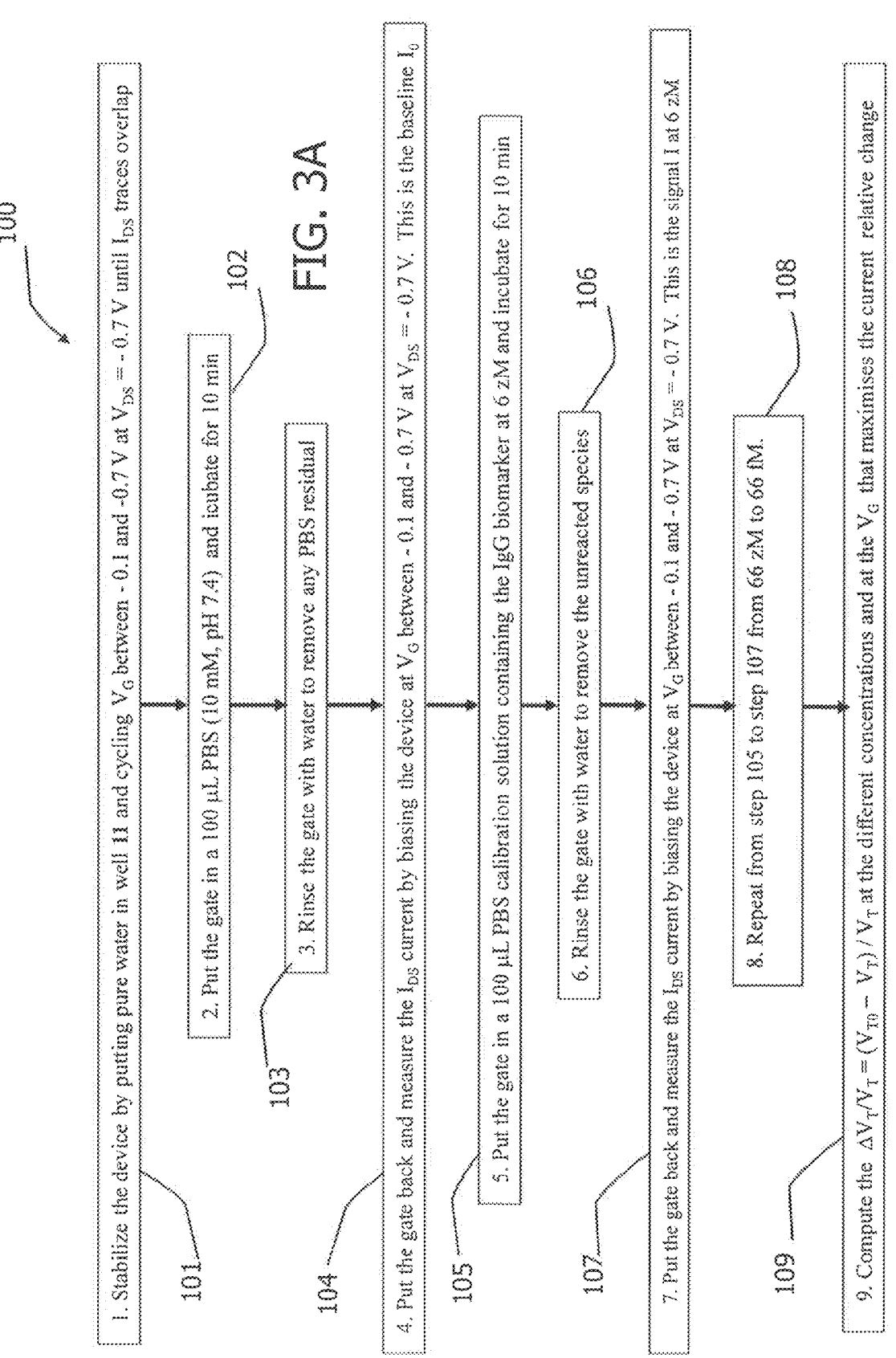

100

1. Stabilize the device by putting pure water in well 11 and cycling $V_G$ between − 0.1 and −0.7 V at $V_{DS}$ = − 0.7 V until $I_{DS}$ traces overlap

101

2. Put the gate in a 100 μL PBS (10 mM, pH 7.4) and incubate for 10 min

102

3. Rinse the gate with water to remove any PBS residual

103

4. Put the gate back and measure the $I_{DS}$ current by biasing the device at $V_G$ between − 0.1 and − 0.7 V at $V_{DS}$ = − 0.7 V. This is the baseline $I_0$

104

5. Put the gate in a 100 μL PBS calibration solution containing the IgG biomarker at 6 zM and incubate for 10 min

105

6. Rinse the gate with water to remove the unreacted species

106

7. Put the gate back and measure the $I_{DS}$ current by biasing the device at $V_G$ between − 0.1 and − 0.7 V at $V_{DS}$ = − 0.7 V. This is the signal I at 6 zM

107

8. Repeat from step 105 to step 107 from 66 zM to 66 fM.

108

9. Compute the $\Delta V_T / V_T = (V_{T0} − V_T) / V_T$ at the different concentrations and at the $V_G$ that maximises the current relative change

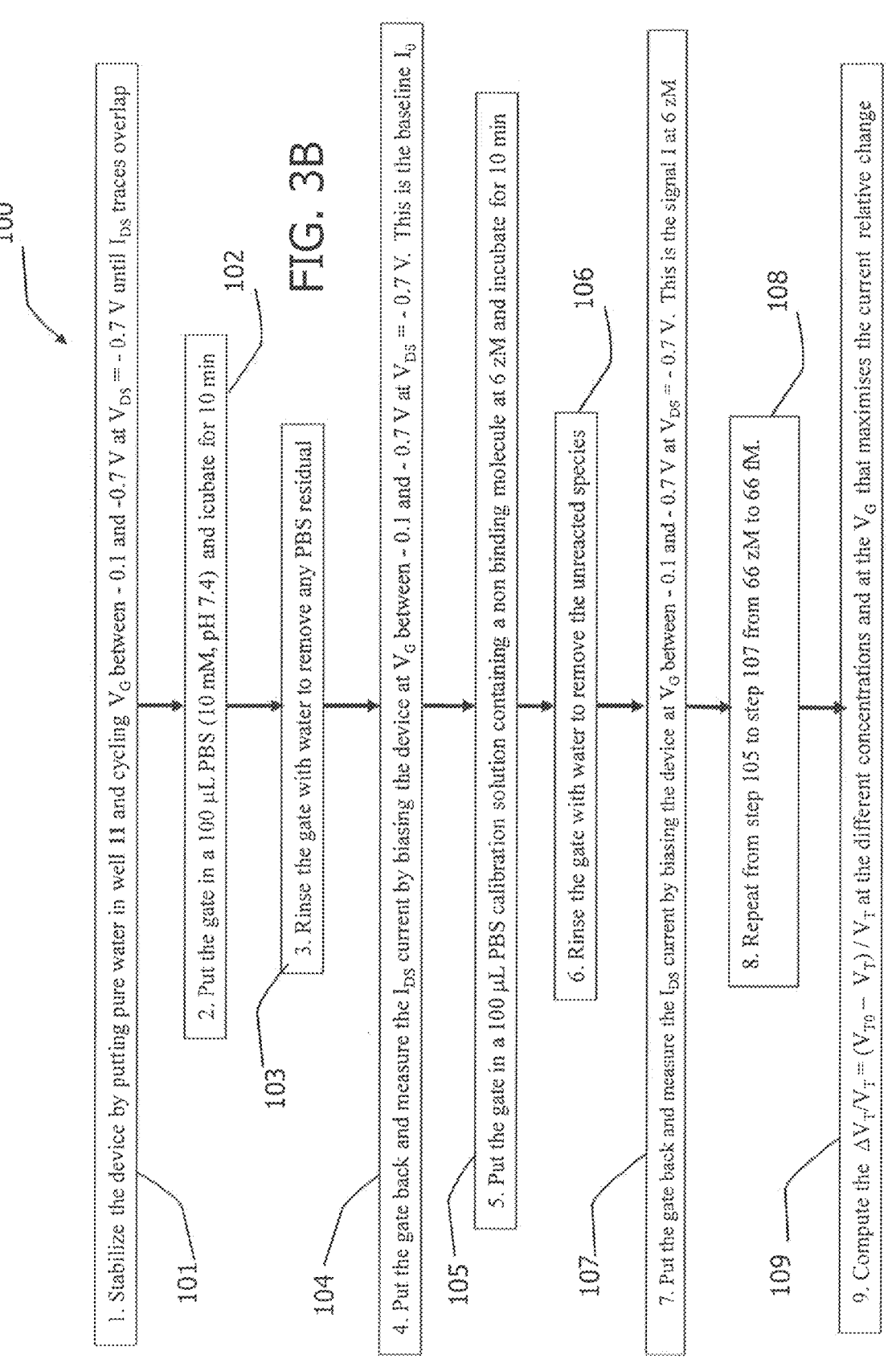

FIG. 3B

1. Stabilize the device by putting pure water in well 11 and cycling $V_G$ between - 0.1 and -0.7 V at $V_{DS}$ = - 0.7 V until $I_{DS}$ traces overlap 2. Put the gate in a 100 µL PBS (10 mM, pH 7.4) and icubate for 10 min 3. Rinse the gate with water to remove any PBS residual 4. Put the gate back and measure the $I_{DS}$ current by biasing the device at $V_G$ between - 0.1 and - 0.7 V at $V_{DS}$ = - 0.7 V. This is the baseline $I_0$ 5. Put the gate in a 100 µL PBS calibration solution containing a non binding molecule at 6 zM and incubate for 10 min 6. Rinse the gate with water to remove the unreacted species 7. Put the gate back and measure the $I_{DS}$ current by biasing the device at $V_G$ between - 0.1 and - 0.7 V at $V_{DS}$ = - 0.7 V. This is the signal I at 6 zM 8. Repeat from step 105 to step 107 from 66 zM to 66 fM.

9. Compute the $\Delta V_T/V_T = (V_{T0} - V_T) / V_T$ at the different concentrations and at the $V_G$ that maximises the current relative change Kapton_Anti-IgG_ETH_BSA_IgG 666fM Au_anti-IgG_ETH_BSA_IgG 66zM Au_anti-IgG_ETH_IgG 666fM

METHOD OF FUNCTIONALIZATION OF A GATE ELECTRODE OF A FIELD-EFFECT TRANSISTOR SENSOR

CROSS REFERENCE TO RELATED APPLICATIONS

This application is a national stage filing under section 371 of International Application PCT/IB2017/058065, filed on Dec. 18, 2017, published in English on Jul. 5, 2018 as WO2018/122671A1, and claims priority to European Patent Application No. 16207596.4, filed on Dec. 30, 2016. The entire disclosures of each application are hereby incorporated herein by reference.

FIELD OF THE INVENTION

The present invention relates to field-effect transistor sensors, in particular biosensors.

More to the point, the invention has been developed with particular reference to a method of functionalization of a gate electrode of a field-effect transistor sensor.

PRIOR ART

In the field of biosensors, and particularly of field-effect transistor biosensors, the search for a sensing system capable of detecting biomarkers at the earliest possible stage of a disease is gaining momentum as new technologies allow for more and more sensitive and reliable detections.

So far, however, the methodological approach has been driven by the idea that miniaturizing, to the highest possible limit, the sensing surface of a detector would be the way to proceed. Label-free single-molecule detection has been achieved via nano-systems that can incorporate or host, owing to size constraints, very few biological receptors.

Single DNA detection has been performed by means of a biosensor based on a single carbon-nanotube field-effect transistor. In this transistor, the DNA probe is attached to a point defect of the nano-channel whose conductance is affected by the presence of a complementary DNA target.

Label-free single-molecule detection has been also performed by way of a whispering gallery mode microcavity. The sensing occurs through the plasmon-enhanced field generated in gold nanorods, that notably depends on the nano-objects aspect ratio, orientation and surface roughness.

Platforms based on force spectroscopies (optical and magnetic tweezers, atomic force microscopy) or ion channels and nanopores, rely also on nano-tools to achieve nanoscale spatial localization. These systems inherently funnel a large (a very large, actually) number of biomarkers towards the interaction with very few biological recognition elements. This leads to a sequence of a highly probable single binding detection events. The single event is measurable as it changes a relative large portion of the nano-surface involved in the interaction.

To actually sense a single biomarker that is dispersed in a large volume of a biological fluid (i.e. a biomarker having an extremely low concentration), the binding events become so highly improbable that a nano-sensor would have to wait for an impractically long time to actually detect a few biomarkers. Accordingly, all of the above detection techniques are inherently unable to track few ligands in a biologically relevant medium as required for instance in early biomarkers detection, wherein the ligand concentration is extremely low.

Such nano-systems are also still limited by low reproducibility of the detection events (and the associated results) and production scalability, both being major issues in the transfer of a technological platform into real clinical applications.

Strikingly, biological cells can decode semiochemicals with a single-molecule sensitivity, through the huge number of receptors residing on the surface thereof. Exemplary of this are sperm cells that, in order to locate the egg cell (ovum), are capable of sensing environmental cues relative to the egg cell down to the physical detection limit.

The binding event between a chemoattractant and one receptor initiates the cell orientation towards the increasing semiochemicals gradient pointing to the source.

The more sensitive the cell is, the faster the navigation thereof will be oriented towards the target. Sperm cell can detect as low as 3-4 ligands while a single ion channel linked receptor (e.g. nicotinic acetylcholine receptors) is able to convert a chemical signal into a detectable ionic current.

Notably, for the chemoattractant-receptor interaction cross-section to be sufficiently high, the cell surface must be covered by an extraordinary large number of highly packed receptors.

Bioelectronics represents one of the most promising directions in printable or low cost production electronics and field-effect transistor (FET). Such devices, that can span dimensions from $\mu$m to mm in size, are based on materials such as printable organic semiconductors (OSCs) but also metal oxides like Indium Gallium Zinc Oxide (IGZO), carbon nanotube thin-films as well as graphene. Among the others, organic FET, particularly electrolyte gated ones, have been demonstrated to work as highly performing bioelectronic FET (bio-FET) sensors. Selectivity is achieved by integrating a layer of functional biological recognition elements, directly coupled with an electronic interface. The study of such biological interfaces has provided insights into the conformational changes of the receptor bio-systems, proving also to be a label-free, sensitive and selective biosensing technology. Electrolyte gated sensors exhibit detection limits down to picomolar (10-12 M) and the high repeatability of the sensor responses is characterized by relative standard deviation as low as 3-5% for hundreds of repeated determinations. Up to 104 repeated measurements in sea water were successfully performed with extremely high repeatability. Moreover, sub-femtomolar (10-15 M, fM) detections were achieved with a graphene FET modified with human olfactory receptors 2AG1. It is important to clarify that, taking into account the volumes typically used with bio-FETs (100 $\mu$L), the number of detected ligands has been so far 108 at pM concentration or 105 at fM concentration, therefore the state-of-the-art in electronic label-free sensing is still very far from single-molecule detection.

OBJECT OF THE INVENTION

The object of the present invention is to overcome the above mentioned technical drawbacks. Specifically, the present invention is aimed at providing a FET biosensor capable of detecting biomarkers (e.g. affinity ligands) at extremely low concentrations, and up to few-proteins detection events, which allows early detection of biomarkers in clinical screening.

SUMMARY OF THE INVENTION

The object of the present invention is achieved by a method of functionalization of a gate electrode of a field-effect transistor sensor having the features forming the subject of the claims that follow, which form an integral part of the technical disclosure herein provided in relation to the invention. Specifically, the object is achieved by a method of functionalization of a gate electrode of a field-effect transistor sensor comprising the steps of:

forming a layer of biological recognition elements on a surface of said gate electrode, wherein said layer of biological recognition elements includes a self-assembled structure of one or more specific-binding-pair-forming substances, treating the layer of biological recognition elements with a solution containing a blocking agent to fill vacancies and prevent nonspecific binding in the self-assembled structure, wherein said one or more specific-binding-pair-forming substances immobilized in said layer of biological recognition elements are packed at a density comprised between $0.1 \times 104$ $\mu m$-2 and $10 \times 104$ preferably between $1 \times 104$ $\mu m$-2 and $2 \times 104$ $\mu m$-2 Furthermore, the object is achieved by a field effect transistor sensor including:

a source electrode a drain electrode a FET channel including preferably an interdigitated pattern of gold contacts a semiconductor disposed on said interdigitated pattern a gate electrode having a surface functionalized according to the above method.

BRIEF DESCRIPTION OF THE FIGURES

Further features and advantages of the invention will become apparent from the following description with reference to the annexed figures, provided purely by way of non-limiting example, and wherein.

DETAILED DESCRIPTION OF PREFERRED EMBODIMENTS

Figures 1, 1A:
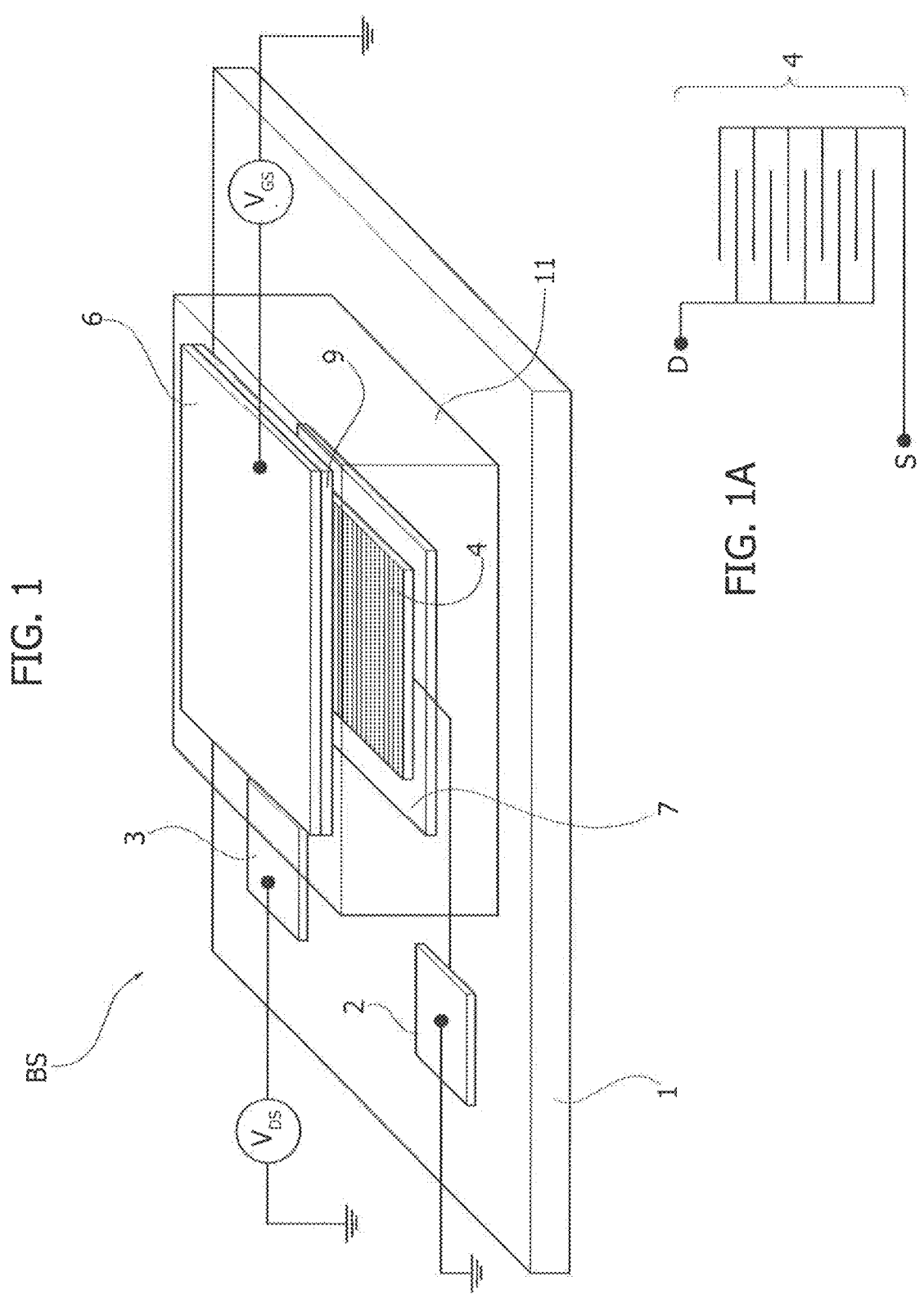
FIG. 1 is a schematic three-dimensional view showing a FET biosensor that can be functionalized by the method according to the invention.
FIG. 1A is a schematic representation of a sub-unit of the biosensor of FIG. 1.

With reference to FIG. 1, the reference BS designates as a whole a FET biosensor featuring a gate electrode functionalized according to the method of the invention.

The biosensor BS includes a substrate 1, preferably made of Si/SiO2. The substrate 1 is flat and non-conductive. Alternatively a glass slide or a flexible plastic substrate such as poliimmide (Kapton®), mica (phyllosilicate, exhibiting a two-dimensional sheet or layer structure), poly(ethylene 2,6-naphthalate) or polyethylene terephthalate can be used.

On the substrate 1, the source (S) and drain (D) electrodes are provided as gold pads made by photolithography and designated, respectively, by reference numbers 2 and 3. The source (S) and drain (D) pads (and the interdigitated electrodes) were defined by electron-beam evaporated gold (50 nm thickness) and a prior deposited layer of titanium (50 nm thickness) serving as adhesion layer. Alternatively, these pads can be defined by screen printing of a conducting ink or thought thermal evaporation of gold trough a shadow mask. Throughout the description, the source and drain electrodes may be referred to as "source pad" and "drain pad" respectively, whether or not in association to the respective reference numbers 2 and 3.

Figures 1B, 1C:
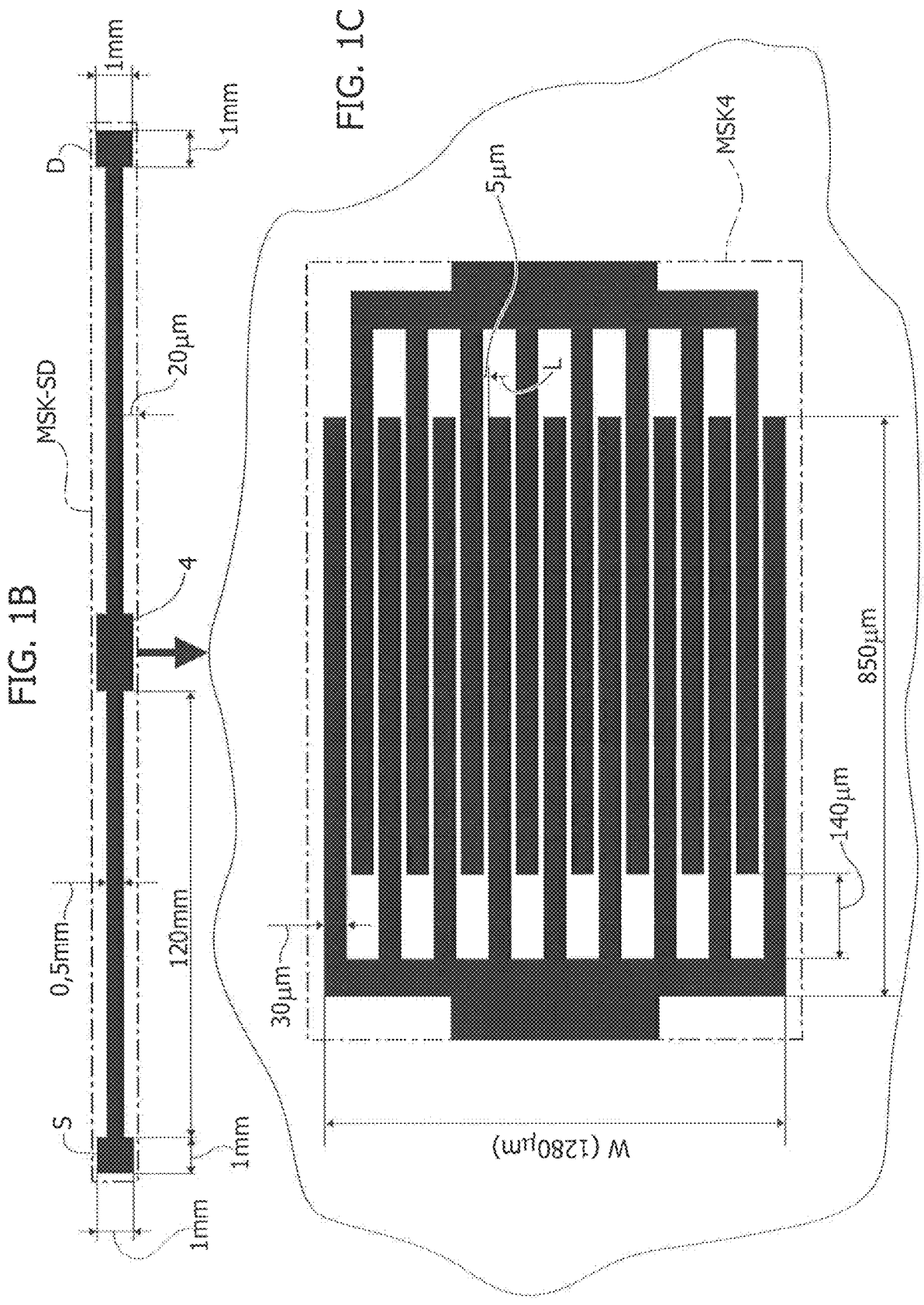
FIG. 1B shows an exemplary pattern of source and drain electrodes in a FET biosensor according to the invention.
FIG. 1C is a magnified view of the channel area of FIG. 1B, corresponding to the sub-unit of FIG. 1A.

The source and drain pads are connected to an interdigitated pattern of gold electrodes 4 that defines the FET channel, a schematic representation of which is provided in FIG. 1A. FIG. 1B provides a more detailed representation of the interdigitated pattern together with some dimensional values of the preferred embodiment, while FIG. 1C offers a magnified view of a portion of FIG. 1B. In the description that follows, such interdigitated pattern will be oftentimes referred to as "interdigitated S and D pattern".

In a preferred embodiment, the interdigitated pattern (FET channel) is 1280 $\mu m$ wide (W, equipotential electrode region) and 5 $\mu m$ long (L, area separating two differently biased regions). Preferably, the interdigitated pattern is defined photo-lithographically as well, similarly to the gold pads 2, 3. The area separating two differently biased regions L may be as large as 5-200 $\mu m$, and can be used with the width W scaled proportionally. L spacing larger than 100 $\mu m$, can also be considered to allow to print or screen mask define the interdigitated pattern.

The interdigitated S and D pattern 4 is further covered by a semiconductor 7 disposed thereon.

Preferably the semiconductor 7 is organic and is made of hydrophobic poly(3-hexylthiophene-2,5-diyl)—or P3HT—exhibiting the following properties: regioregularity >99%, average molecular weight of 17.5 kDa g mol-1. A P3HT solution (2.6 mg ml-1 in 1,2-dichlorobenzene) filtered with a 0.2 $\mu m$ filter was spin-coated at 2,000 r.p.m. for 20 s and annealed at 80° C. for 1 (one) hour. In the preferred embodiment, the total semiconductor area is 6.5 10-3 cm-2.

The P3HT surface is highly hydrophobic as the contact angle is as high as 103±3°. Alternatively, poly[2,5-bis(3-tetradecylthiophen-2-yl) thieno[3,2-b]thiophene] (PBTTT-C 14), poly(2,5-bis(3-hexadecylth-iophene-2-yl)thieno[3,2-b] thiophene (pBTTT-C16), pBTTT-C14 as well as solution processed pentacene, graphene, can also be used as a material for the semiconductor 7.

Specifically, PBTTT-C14 can be dissolved (7 mg/ml) in a mixture of 1,2-dichlorobenzene and chloroform (in 9:1 ratio). PBTTT-C14 solution can be spin deposited at 7,000 r.p.m. for 60 s and annealed at 120° C. for 10 min.

The FET biosensor BS further includes a gate electrode 6, which in the preferred embodiment is a gold platelet with an area of 0.6 cm2 that hangs stably over the FET channel area. Alternatively, the gate electrode 6 can be defined by thermal evaporation or electron beam deposition of Ti (50 nm) and Au (50 nm) as well as by printing on a flexible substrate such as poliimmide, mica, poly(ethylene 2,6-naphthalate) or polyethylene terephthalate, but also on rigid substrates such as Si/SiO2.

Figure 2:
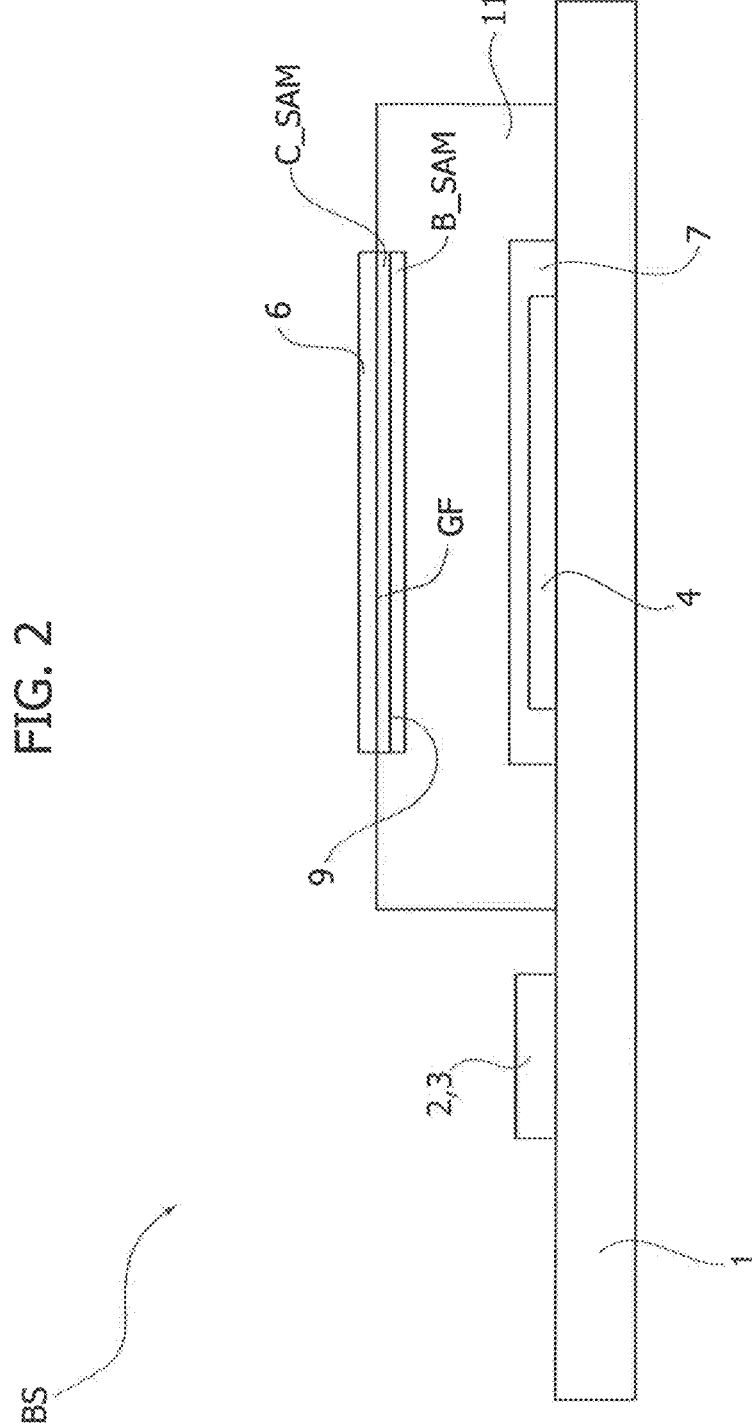
FIG. 2 is a bi-dimensional view showing the FET biosensor of FIG. 1, FIG. 3 illustrate flow charts showing functionalization and measurement steps in combination according to the invention, particularly to measure the IgG affinity ligand (FIG. 3A) and a related negative control experiment (FIG. 3B).

The gate electrode 6 includes a surface 6F (FIG. 2) which in the FET shown in the figures is exposed to and faces the semiconductor 7 covering the interdigitated S and D pattern 4. A well 11 is provided to delimit the interdigitated S and D area, wherein the well 11 is filled with pure HPLC-grade water which serves as electrolyte to operate the biosensor BS, which is functionally an electrolyte-gated FET (EG-FET), and to perform the sensing measurements. Diluted salt solutions can also be used. The surface 6F faces the well 11 and is exposed to the gate electrolyte contained therein.

According to the invention, the surface 6F is bio-functionalized by forming a layer of biological recognition elements 9 thereon. Said layer of biological recognition elements 9 includes one of:
    a complex of a chemical self-assembled structure and a biological self assembled structure of one or more specific-binding-pair-forming substances, wherein the biological self-assembled structure is chemically grafted onto the chemical self assembled structure, or
    a biological self assembled structure of one or more specific-binding-pair-forming substances, wherein the structural units of the biological self assembled structure are treated to exhibit grafting properties in respect of the substrate they are intended to graft on i.e. the gold surface of the gate electrode 6.

In the preferred embodiment, the layer of biological recognition elements 9 includes a chemical self assembled monolayer (chemical SAM, C_SAM in the figures) and a biological self-assembled monolayer (biological SAM, B_SAM in the figures) of one or more specific-binding-pair-forming substances.

According to the invention, said one or more specific-binding-pair-forming substances include one or more of the following:
    antibodies (one or more) against a selected bio-marker,
    anti-human Immunoglobulin (anti-hIG) antibodies,
    anti-human Immunoglobulin G (anti-IgG) antibodies,
    anti-human Immunoglobulin M (anti-IgM) antibodies,
    specific-binding-pair-forming substances for dopamine, chiral odors, DNA, human glycoprotein, inflammatory cytokines, C-reactive proteins.

In embodiments only featuring a biological self assembled structure, the same is a self assembled monolayer of one or more specific-binding-pair-forming substances with a thiol group able to spontaneously attach to the gold surface such as, but not limited to, proteins modified in such a way as to have an exposed cysteine. Direct physical adsorption of capturing proteins is also considered.

In the preferred embodiment, the gate electrode functionalization method according to the invention provides that a SAM layer B_SAM of anti-human Immunoglobulin G (anti-IgG, preferred) or anti-human Immunoglobulin M (anti-IgM) antibodies be added covering the whole gate surface, and specifically be grafted onto a chemical SAM layer C_SAM applied to the surface 6F of the gate electrode 6 to be functionalized. Clearly, the invention can be practiced with other specific-binding-pair-forming substances (e.g. a selected antibody for a target biomarker).

The protein SAM deposition procedure is general as it does not depend on specific features (such as for instance functional groups) that are characteristics solely of the antibodies. This renders the deposition method extendable i.e. to all of the biological species mentioned above (all the antibodies, PNA, human glycoprotein, or proteic receptors for dopamine, chiral odors, inflammatory cytokines, C-reactive proteins). This is an essentially general platform for immunoassay.

According to the invention, the one or more specific-binding-pair-forming substances (such as for instance anti-hIg, anti-IgG, anti-IgM but also antibodies in general) immobilized in the layer of biological recognition elements 9 (particularly in the biological SAM) are packed at a density comprised between $0.1 \times 104$ μm-2 and $10 \times 104$ μm-2, preferably between $1 \times 104$ μm-2 and $2 \times 104$ μm-2.

In the preferred embodiment, it is estimated that up to 1012 of anti-IgG are immobilized on the 0.6 cm2 gate surface, corresponding to a density of $1.6 \times 104$ μm-2 proteins per μm2.

In the preferred embodiment, the chemical SAM C_SAM on the surface 6F of the gate electrode 6 is produced by first cleaning the gold platelet (gate electrode 6) as follows:
    first, the gold platelet is Bunsen burnt (flame annealed) for 5 seconds and immersed in a piranha solution [H2SO4 (97% v/v) and H2O2(30% v/v) 3:1 v/v] for 20 min afterwards. The flame annealing can last for about 20 seconds, while the immersion in the piranha can last for 10-30 minutes.
    then, the platelet is kept in boiling water for 10 minutes, then treated for 10 min in an ozone cleaner.

Alternatively, the gate electrode surface can be polished by a cyclic voltametry based technique, commonly termed as 'electrochemical polishing'. Cyclic-voltametry polishing can be carried out in three electrodes configuration using an electrochemical analyzer.

Ag/AgCl electrode in KCl solution is used as reference electrode, 0.5 M sulfuric acid (H2SO4(97% v/v)) can be used as electrolyte in the electrochemical cell. The gate electrode 6 is placed as working electrode held in the solution using a standard electrode holder.

A platinum plate of relatively large area, approximately 10 times larger than that of the gold working electrode 6 serves as control electrode. The potential is scanned between 0V to +1.5 V for at least 30 cycles. The scan rate is maintained at 0.1 V/s. Before every measurement, the electrolyte solution can be replaced with fresh solution and N2 is bubbled through the electrolyte for at least 10 minutes to remove the dissolved oxygen contents.

After electrochemical polishing, the gate electrode 6 is thoroughly rinsed with ultra-pure HPLC grade water and then with ethanol, and dried under a gaseous nitrogen (N2) stream.

Alternatively, the gate electrode 6 can be defined as a thin film, by thermal evaporation or electron beam deposition of Ti (50 nm) and Au (50 nm) as well as by printing on a flexible substrate such as poliimmide, mica, poly(ethylene 2,6-naphthalate) or polyethylene terephthalate, but also on rigid substrates such as Si/SiO2. This gate does not need any cleaning procedure and is directly processed for bio-functionalization starting from the step described in the following.

After the flame annealing or the electrochemical polishing of the gate electrode, or directly for the gate made of a thin-film of gold, in the preferred embodiment the chemical SAM layer is added to the gate electrode 6 by means of a precursor consisting of a layer of alkanethiols terminating with carboxylic functionalities, which is deposited on the surface 9. To this end, a 10 mM solution consisting of 10:1 ratio of a 3-mercaptopropionic acid (3-MPA) to 11-mercaptoundecanoic acid (11-MUA) was prepared in ethanol grade, puriss. p.a. assay, >99.8.

The cleaned gold platelet was immersed in the 3-MPA and 11-MUA solution and kept in the dark (i.e. in the absence of visible and UV light) under constant gaseous nitrogen (N2) flow for eighteen (18) hours at 22° C.

The inventors have however observed that, in addition to the preferred parameters above, the same step can be practiced with a solution having a concentration in the range 10 mM to 100 mM, consisting of a 10:1 to 1:1 ratio of a 3-mercaptopropionic acid (3MPA) to 11-mercaptoundecanoic acid (11 MUA) in ethanol grade, but also composed by the sole 3-mercaptopropionic acid, and immersing the gate electrode 6 therein for a residence time comprised between 15 and 20 h and at a temperature of 15 to 24° C.

The strong gold-sulfur interaction results in the exposure of the carboxylic groups, activated subsequently by reacting the partially processed gate electrode as per the above in a 200 mM 1-Ethyl-3-(3-dimethylaminopropyl)carbodiimide (EDC) and 50 mM sulfo-N-Hydroxysuccinimide (sulfo-NHS) aqueous solution for two (2) hours at 25° C.

Again, the inventors have however observed that, in addition to the preferred parameters above, the same step can be practiced by reacting the gate electrode 6 in a 50 mM to 250 mM 1-Ethyl-3-(3-dimethylaminopropyl)carbodiimide (EDC) and 50 mM to 250 mM sulfo-N-Hydroxysuccinimide (sulfo-NHS) for a residence time comprised between 1 and 3 h and at a temperature of 22 to 26° C. An N-Hydroxysuccinimide (NETS) aqueous solution can be used instead of the sulfo-NHS one.

In the preferred embodiment, the anti-human Immuno-globuline G (anti-IgG) or the anti-human Immunoglobuline M (anti-IgM) SAM layer (biological SAM) is thus generated through the anchoring of the antibodies (or generally of the specific-binding-pair-forming substance) to the chemical SAM C_SAM, specifically to the carboxy groups linked to the sulfo-NHS or to the NETS moyeties resulting from the chemical activation described in the previous paragraph, by immersing the gate electrode 6 in a Phosphate Buffered Saline (PBS) solution containing the antibodies for two (2) hours at 25° C.

According to the invention, the Phosphate Buffered Saline (PBS) solution may consist of 0.1-1 mg ml-1 of antibodies such as, but not limited to, anti-IgG or anti-IgM and 5 mM to 25 mM of phosphate buffer having a pH in the range 5 to 8 and a physiologically relevant ionic strength in the range 10 mM to 200 mM.

In the preferred embodiment, the solution consists of 0.7 µM (0.1 mg ml-1) of antibodies and (forse in?) PBS made by 10 mM phosphate, KCl 2.7 mM and 137 mM NaCl having a pH of 7.4 and a ionic strength of 162 mM.

Once again, the inventors have however observed that, in addition to the preferred parameters above, the same step can be practiced by immersing the gate electrode 6 in a buffer solution comprising anti-IgG antibodies or anti-IgM antibodies (other antibodies in general), wherein the buffer solution comprises one of:

Na phosphate buffer solution of Dulbecco's phosphate buffered saline (D-PBS, KCl: 2.7 mM, NaCl: 136 mM, KH2PO4: 1.5 mM, Na2HPO4: 8.1 mM)

Phosphate buffer solution 20 mM and pH 8 for a residence time comprised between 15 min to 3 h and at a temperature of 23 to 26° C.

Moreover, the antibody solution (anti-IgG, or the anti-IgM for example) shall have optimal pH and ionic strength depending on the source of antibodies.

Suitable pH values are in the range from 5 to 9 and ionic strength from 10 mM to 200 mM.

Other buffers that can be used to practice the method according to the invention include (depending on the desired pH value): Tris-HCl, phosphate, citrate, imidazole—Cl, PIPES, ACES MOPSO, BES, TES, MOPS, DIPSO, TAPSO, HEPPSO, POPSO, TEA, EPPS, Tricine, Glycine, Bicine, HEPBS, TAPS, AMPD, Borate.

The ionic strength can be adjusted by any salt that does not interfere with the covalent attachment of the antibody to the gate and with the native conformation of the antibody. Commonly used salts are NaCl and KCl.

Alternatively, the following protocols can be used to attach different biological recognition elements that will endow the biosensor BS (specifically when the same is embodied as a EG-OFET) of a good degree of selectivity. Namely for instance:

a SAM from cystamine 1 mM aqueous solution with subsequent covalent immobilization of 4-formylphe-nylboronic acid saturated in 1,4-dioxan at 40° C. for 2 h to detect dopamine.

The physical adsorption of: histidin-tagged protein G (5 mg/mL) in PBS (100 mM of PBS, pH 7.4) to attach IL4 monoclonal antibody (0.25 mg/mL anti-IL4) for 1 h at 5° C. to detect interleukin-4.

A SAM functionalization: 50 mM solution of 3-mercaptopropionic acid (3MPA) in ethanol containing 5% acetic acid under nitrogen, in the dark for 18 h at 22° C. Activation: 100 mM EDC and 200 mM NHS aqueous solution for 1 h at 25° C. Covalent immobilization of odorant binding proteins, pOBPs, [SEP] (0.7 mg ml -1 in 20 mM Na phosphate buffer, pH 8.0), 2 h at 25° C., to detect chiral odors such as carvone.

Covalent immobilization: reduced thiolated ssDNA-probes (7 pmol/cm2), on floating gate electrode in Tris buffer (10 mM Tris, 1 mM EDTA, pH 8.0) at 0.1 M NaCl for 2 h. Rinsed with Tris without NaCl.

SAM: 10-carboxy-1-decanethiol (1 mM in hexane) 1 h, room temperature. Washing with ethanol and water. Activation: 5 µl 2-morpholino-ethane-sulfonic acid buffer solution (MES, 100 mM, pH 6.0) containing 5 mM sulfo-NHS, N,N'-di-isopropyl-carbodiimide (DIC, 40 mM) and sodium chloride (500 mM), 15 min. Covalent immobilization: Streptavidin (500 µg/ml) in 5 µl of a carbonate buffer solution (Na2CO3: 15 mM, NaHCO3: 35 mM, pH 9.6) on electrode, 15min. Physical adsorption: immersion in D-PBS containing 0.05 wt. % Tween 20, 0.1 wt. % BSA, 15 min.

SAM: 5-carboxy-1-pentanethiol. Activation: 5 µl 2-morpholino-ethane-sulfonic acid buffer solution (MES, 100 mM, pH 5.5) containing 5 mM sulfo-NHS, DIC (40 mM), 15 min. Covalent immobilization: Streptavidin (500 µg/ml) in 5 µl of a carbonate buffer solution (Na2CO3: 15 mM, NaHCO3: 35 mM, pH 9.6) on electrode, 2 h, room temperature. Physical adsorption: immersion in D-PBS containing 0.05 wt. % Tween 20, 0.1 wt. % human serum albumin (HMS), 15 min. Incubation in biotin-tagged anti-CgA antibody (30 µg/mL) with 0.1 wt % HSA PBS solution, 30 min, room temperature.

Once the anti-IgG or the anti-IgM SAM B_SAM is set in place there is the need to "block" the bio-functionalised layer 9 (this applies to whatever specific-binding-pair-forming substance the SAM is made of). Specifically, the layer of biological recognition elements 9 is treated with a solution containing one or more blocking agents to fill vacancies and prevent nonspecific binding in the self-assembled structure.

In the preferred embodiment, this is performed via saturation of the unreacted activated carboxy groups of the functionalized chemical SAM layer, particularly by means of concentrated solutions of amines for a time long enough to allow the reaction with all the activated carboxylic groups (usually from 30 min to few hours). The amines can be supplied as additive in a buffer (such as ethanolamine 1 M in PBS) or can be the rinsing buffer itself (such as Tris).

To this end the anti-IgG or anti-IgM layer in the preferred embodiment is treated with ethanolamine 1 M in PBS for one (1) hour at 25° C.

Finally, the bio-functionalized gate electrode 6, particularly the layer 9, is immersed in a 1.5 µM (0.1 mgml-1) BSA (Bovine Serum Albumine) solution in PBS 10 mM for one (1) hour at 25° C. Therefore, in the preferred embodiments ethanolamine and BSA are used as blocking agents.

The inventors have however observed that the blocking step can be practiced by immersing the bio-functionalized gate electrode 6, particularly the layer 9, in a 0.05 to 1 mg ml-1 BSA solution in buffer at pH=7.4 composed by phosphate 5 mM to 20 mM and at ionic strength ranging from 80 mM to 350 mM for a residence time comprised between 30 min and 2 h, and at a temperature comprised between 22° C. and 26° C.

Alternatively, other blocking agents include Human Serum Albumin (0.01-3% W) Tween 20, casein or 1 mM 6-mercaptohexanol (MCH), 2-aminoethanol (1 M) in 5 µl of Dulbecco's Phosphate Buffered Saline (D-PBS, KCl: 2.7 mM, NaCl: 136 mM, KH2PO4: 1.5 mM, Na2HPO4: 8.1 mM). The exposure (residence time) to these solutions can vary from 15 minutes to 3 hours.

The "surface blocking" step as described above is generally carried out to minimize the non-specific binding. The inventors have also noted that, when performed in a method according to the invention, such a step can also drastically improve the sensitivity of the biosensor BS. The molecules used to "block the surface" minimizes non-specific adsorption of biomolecules to the gate electrode areas that are not fully covered by the anti-IgG or the anti-IgM (or more in general by antibody proteins). Additionally, the BSA also works as—so to say—a mechanical and electrostatic coupler for the biological self assembled structure.

While in prior art of functionalization methods the physically adsorbed BSA is used to maximize the specificity of the response of the biosensor, in the method according to the invention, the addition of physically adsorbed BSA allows to dramatically improve the biosensor BS sensitivity as will be further described.

In between each of the above steps of the bio-functionalization method according to the invention, the gate electrode 6 is rinsed thoroughly to remove any possible residues.

Figure 4:
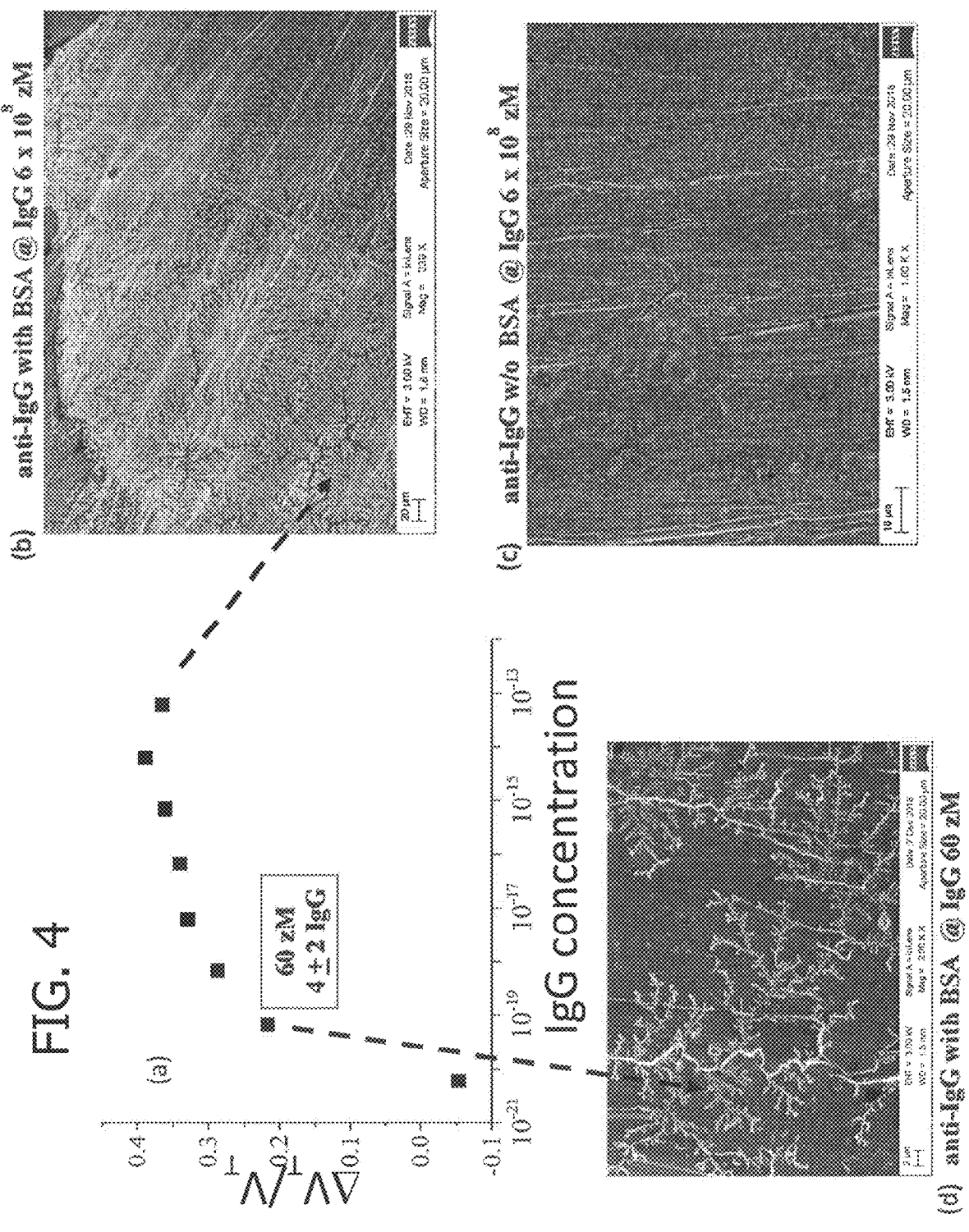
FIG. 4 is a multiple plot showing the relative threshold voltage change as a function of ligand concentration along with representative scanning electron micrographs of the gate surface at the different sensing stages.

In the preferred embodiment, the sensing measurements are performed by exposing anti-IgG or the anti-IgM functionalized gate to selectively detect IgG or IgM respective affinity ligands according to the sequence of steps in the flow chart 100 of FIG. 3. This sequence of steps i.a. resulted in the data displayed in the plot of FIG. 4.

The measurement method of FIG. 3A first envisages to stabilize the biosensor BS. The gate electrode is stably put at a distance of about 3-5 mm from the surface of the semiconductor 7. Also, 300-1000 µL HPLC-grade water, is put in the well 11 and cycling the gate-source voltage VGS between −0.1 and −0.7 V with the drain-source voltage VDS set at −0.7 V until the drain current (channel current) IDS traces overlap (step 101).

The SAM in water is charged due to the presence, upon application of the gate bias, of a Debye length of 20-200 nm, therefore larger than the SAM height (ca. 20 nm). This allows the FET detection to affectively traces electrostatic and capacitive changes occurring in the BS. In particular, the FET threshold voltage shift can quantitatively account for the presence of a fixed dipole moment associated with the SAM or with the complex attached to the gate electrode surface.

Next, step 102, it is envisaged to put the gate electrode 6 functionalized by the method according to the invention in a 100 µL PBS, and incubate the same for ten (10) minutes. Incubation time can vary from 1-30 minutes.

Then, step 103, the gate electrode 6 is washed with HPLC water to remove any PBS residue.

After that, step 104, the gate electrode 6 is put back onto the biosensor and the drain current (channel current) IDS is measured by biasing the biosensor BS with a gate-source voltage VGS between −0.1 and −0.7 V with the drain-source voltage VDS set at −0.7 V. The measured drain current vs. VGS (transfer curve) is the baseline I0.

From the sqrt(IDS) vs. VGS, following the standard FET equation (in the VDS saturation region), IDS=(W/2L gET Ci (VGS−VT)2)], it is possible to extract the values for VT and µGET Ci. µFET is the semiconductor field effect mobility (that can range between 10-3 and 102 cm2 V-1 sec-1, depending from the semiconductor) while Ci is the gating capacitance of the FET. After the semiconductor stabilization and hence the interfacial traps are filled, the extracted VT quantifies the work function of the gate, referred to that of the semiconductor. As the latter is invariant during the sensing, changes in VT are to be ascribed to electrostatic changes occurring in the gate SAM. No capacitance changes are expected in the present invention because the gate surface area (0.6 cm2) is two orders of magnitude larger than the surface area of the channel semiconductor (0.006 cm2). Considering that the thickness and the relative dielectric constant of the biological SAM B_SAM attached to the gate and of the two-dimensional FET channel induced in the semiconductor are comparable, the capacitance of the FET channel is the lowest in the series of capacitances gating the system. The total capacitance is invariant to the changes induced in the biosensor upon interaction with the affinity ligands, therefore the gating capacitance Ci is fixed. No changes of gET (charge carrier mobility due to field effect) occurs as well. So only VT changes.

In step 105 the gate electrode 6 is put in a 100 µL PBS calibration solution containing the IgG (biomarker or affinity ligand) or the IgM (ligand) at 6 zM (6·10-21) nominal concentration, and the same is incubated for ten (10) minutes.

Then, step 106, the gate electrode 6 is washed with water to remove the unreacted species.

Next, at step 107, the gate electrode 6 is put back onto the biosensor and the drain current (channel current) IDS is measured once again by biasing the biosensor BS with a gate-source voltage VGS between −0.1 and −0.7 V with the drain-source voltage VDS set at −0.7 V. The measured IDS current is the signal, I, at 6 zM.

Step 108 further envisages to repeat steps 105 to 107 by sweeping through all the range going from 66 zM to 66 fM nominal concentrations. Following this, the same measurement set is repeated with a non-binding ligand, as a negative control. The IgM is the not binding ligand (negative control) for the anti-IgG, while the IgG is the not binding ligand for the anti-IgM.

At step 109, when all of the data are collected, the relative change of the VT (extracted from the transfer curves) variation ($\Delta VT/VT0$) is measured, which is defined as:

$$(\Delta VT/VT0) = (VT0 - VT)/VT$$

is the normalized threshold voltage response at a given concentration. The data are reported in FIG. 4. The threshold voltage, VT, shifts towards more negative potentials upon incubation of the anti-IgG functionalized gate in solutions containing its affinity ligand, IgG, at different concentrations is reported. The same occurs for the anti-IgM exposed to IgM in the same concentration range (data not shown).

Indeed, no response is recorded when the anti-IgG gate is incubated in a IgM (an antibody that does not bind to anti-IgG) solution or when an anti-IgG gate is incubated 9 times in a bare PBS solution for 10 minutes each incubation. No response is observed also when the anti-IgM is exposed to IgG or when the anti-IgM gate is incubated for 9 times consequently in a PBS solution for 10 minutes at each exposure. The data relevant to the anti-IgM and relevant to all the negative control experiments are not shown.

The biosensor BS shows a response to IgG at concentrations above $60\pm24$ zeptomolar ($10$-$21$ M) concentration with more than 20% relative VT change. In 100 µL at this nominal concentration there is 68.3% probability to find $4\pm2$ proteins.

The experimental evidence described above, clearly shows that the biosensor BS, featuring a gate electrode 6 functionalized according to the invention, is capable of detecting two to six proteins despite the fact that the gate electrode is millimetric in scale and hosts trillions ($10^{12}$) of anti-IgG receptors.

In FIG. 3B the same procedure as for FIG. 3A is envisaged, but the assay involves a target molecule that it is not the affinity ligand for the protein immobilized on the gate electrode. Therefore, this is a negative control experiment, namely an experiment that has to result in a zero response (for this reasons reference numbers have been maintained identical to those previously referred to).

Figure 6:
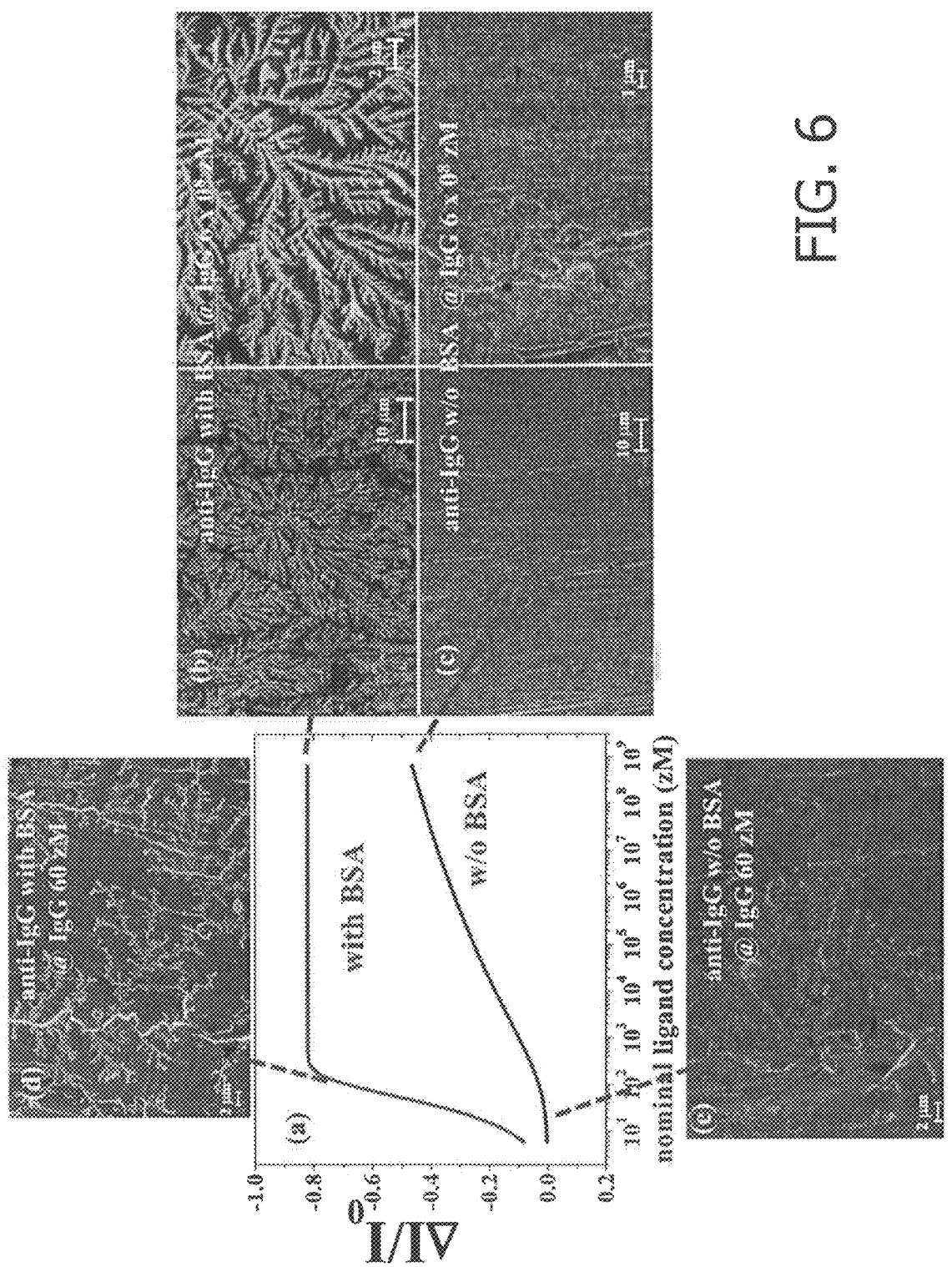
FIG. 6 is a comparative plot showing the dose-response curves, i.e. the relative current change as a function of ligand concentration (sensing signal), of a biosensor functionalized according to the invention, along with representative scanning electron micrographs of the functionalized gate surface.

FIG. 6: The Role of BSA in Sensing Down to $4\pm2$ IgG Proteins

Panel (a) shows the modelling described in the next paragraph of the binding curves (experimental data not shown) gathering the $\Delta I/I0$ data points measured with different EG-OFETs. Upper curve is representative of a fully BSA blocked anti-IgG-SAM gate exposed to the IgG ligand solution spanning nine orders of magnitude in concentration.

The lower curve is representative of the response to IgG, in the same concentration range, of an anti-IgG gate electrode that was not blocked with BSA (prior art biosensor).

All the data that have been modelled are averaged over three replicates measured on different anti-IgG SAM gates and on different P3HT OFET devices with the reproducibility error (taken as one standard deviation) being as low as 8.4% at most. The relative current variation in the IgM negative control assay taken as the level of the blank, was as low as $3.6\pm3.8\%$. The limit of quantification (LOQ), taken as the average of the blank signal plus ten times the blank standard deviations, is 40 zM for the anti-IgG gate with BSA and as high as $1\times108$ zM for the gate without BSA. In panel (b) and (c) the SEM images (at different level of magnification) of the anti-IgG gate with and without (w/o) BSA after the measurement of the whole calibration curve reported in panel (a). In panel (d) the fully BSA blocked anti-IgG gate exposed to IgM till a concentration of $6\times108$ zM, is reported. The paned (e) and (f) report the morphology of an anti-IgG gate with and without BSA exposure to the sole 6 zM and 66 zM concentrations. Despite only $4\pm2$ ligands are present in the solution, the anti-IgG with the BSA show a remarkable coverage of dendritic structures that are visible in the tens of micrometers range.

Model Shown in FIG. 6

Let's consider a gate that is uniformly covered by a number of n of highly packed ($\sim104$ µm-2) binding sites, that can be as high as 1012 in the case of anti-IgG antibodies attached on the gate with an area of 0.6 cm2. The presence of defects in the anti-IgG SAM defines a number of domains within which a given conformational change can freely propagate. The BSA can "block" these defects and act as an electrostatic/mechanical coupling agent that allows a given domain to extend beyond a border defined by the originally present defect. Assuming that the probability for a number k of affinity ligands (IgG in this case) to interact with a binding site (anti-IgG) follows a Poisson distribution, the probability for the k ligands to actually interact is:

$$P_k = \frac{\lambda^k e^{-\lambda}}{k!} \tag{1}$$

where $\lambda$ is the average number of affinity ligands per binding site. Assuming N as the number of ligands in the volume V of an incubation solution at a nominal concentration c (M), hence:

$$\lambda = \frac{N}{n} = \frac{cVN_A}{n}. \tag{2}$$

NA being the Avogadro's number. Analogously, the probability that a given binding site does not interact with any ligand is:

$$P_0 = e^{-\lambda} \tag{3}$$

Each domain, depending on its size, can be assumed to contain a number x of binding sites. Under the assumption that the probability of interaction of each of the k ligands with each of these sites is mutually independent (i.e. the binding affinity is non cooperative), the probability $f_0(x, \lambda)$ that none of these domains interact with anyone of the k ligands, is given by the product of the probabilities for each site to remain empty, so that:

$$f_0(x, \lambda) = \prod_1^x P_0 = P_0^x = e^{-\lambda x}. \tag{4}$$

If the number of binding sites, x, in each domain is distributed according to a probability distribution function $\Psi(x)$, the overall probability of finding a domain of binding sites that has not interacted with any ligand upon exposure to the N ligands present in the incubation volume V, can be evaluated by means of the following integral:

$$f_0(\lambda) = \int_1^{10^{12}} \Psi(x)e^{-\lambda x}dx \approx \int_0^{\infty} \Psi(x)e^{-\lambda x}dx. \tag{5}$$

If the higher limit of integration is reasonably approximated to infinite and the lower one to zero, the probability $f_0(\lambda)$ in Eq. 5 becomes the Laplace Transform of the distribution function of the number of binding sites of a given domain $\Psi(x)$. Under these approximations, $\Psi(x)$ becomes the domain size distribution function. Eventually, the probability that a domain interacts with at least one ligand is:

$$f_{k \geq 1}(\lambda) = 1 - f_0(\lambda). \tag{6}$$

As each data point, $\Delta I/I$ is proportional to the number of anti-IgG domains in which the conformational transition has been triggered by the contact with at least one IgG ligand, the following holds:

$$\frac{\Delta I}{I_0} = A_{sat}(1 - f_0(\lambda)). \tag{7}$$

with Asat being the $\Delta I/I$ saturation value. The dependence of $\Delta I/I$ from c is not lost, as according to Eq. 2, $\lambda$ is proportional to the ligands nominal concentration c. Moreover $\Psi(x)$ can be obtained from the inverse Laplace Transform of the experimental data $\Delta I/I$ set in the A, domain. This will allow to actually fit the data of FIG. 4, but the inversion of the Laplace Transform is ill-conditioned and, although several alternative numerical methods have been proposed (Štěpánek, P., "Data Analysis in Dynamic Light Scattering, in Dynamic Light Scattering: The Method and Some Applications" Chapter 4, author Brown, W. Ed., Oxford Science Publications, Clarendon Press, Oxford, UK: 1993), the use of a model function to fit the experimental data in $\lambda$, is here preferred. Assuming for $\Psi(x)$ a unimodal gamma-distribution with its characteristic shape (b) and scale (K) parameters, (Weisstein, E. W. in *CRC Concise Enciclopedia of Mathematics*, Chapman & Hall/CRC, New York, 1999, p. 694.), it results:

$$\Psi(x) = \frac{x^{b-1}}{K^b} \frac{\exp\left(-\frac{x}{K}\right)}{\Gamma(b)} \tag{8}$$

where $\Gamma(b)$ is the gamma function, allows to define the average value as Kb and the standard deviation as bK2. Furthermore, a definite mode exists only for b>1 and equals (b−1) K. The advantage of this assumption is twofold: in the x-domain, this distribution can describe both a symmetrical and an asymmetrical distributions and its Laplace transform in the $\lambda$-domain is simply:

$$f_0(\lambda) = (1 + K\lambda)^{-b} \tag{9}$$

so that:

$$\frac{\Delta I}{I_0} = A_{sat}(1 - (1 + K\lambda)^{-b}). \tag{10}$$

Figure 5:
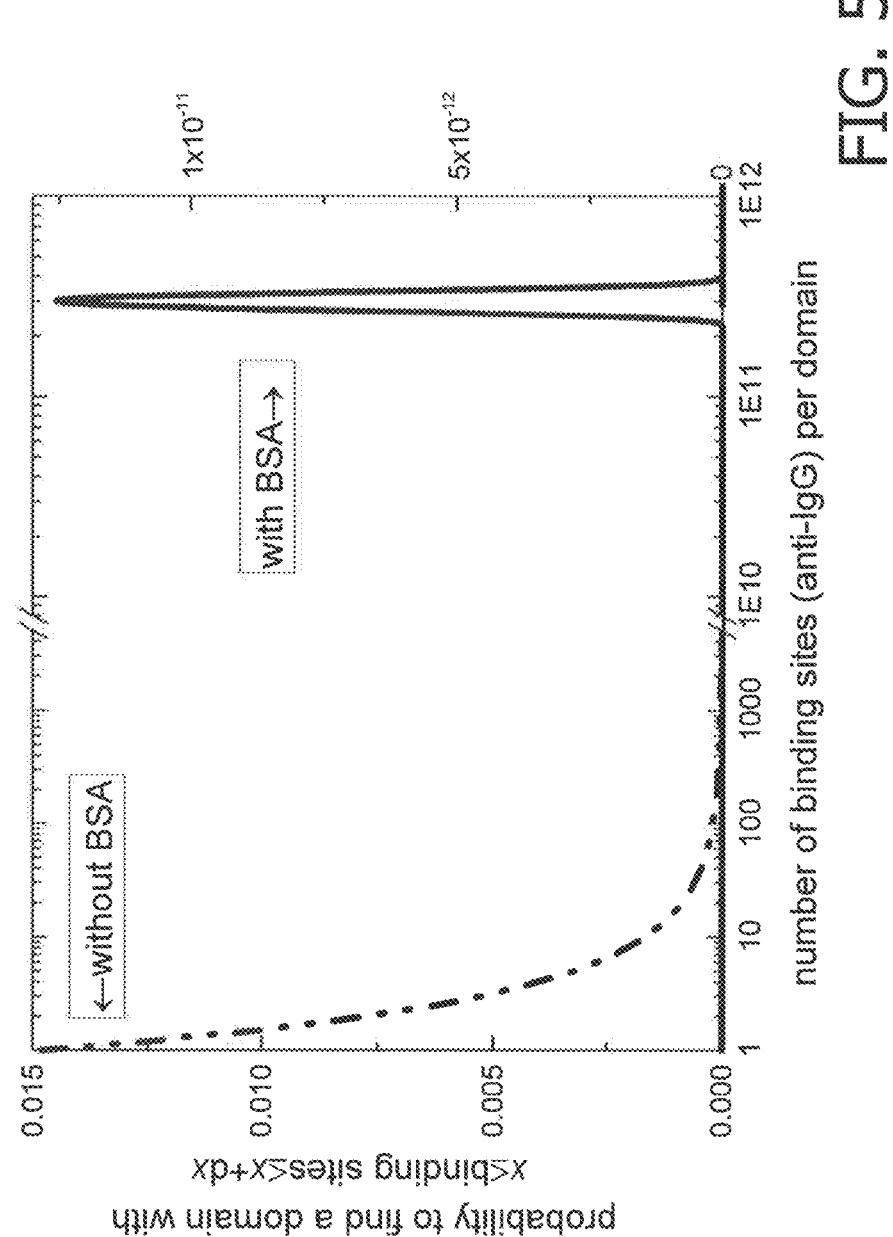
FIG. 5 shows plots of probability density functions, specifically associated to the overall probability of finding a domain of binding sites that has not interacted with any ligand upon exposure to N ligands present in an incubation volume V. Here the Gamma-distribution, $\Box(x)$ vs. the number of binding sites, x, that best describes the dose-response curves, for an anti-IgG SAM with and without BSA deposition.

Eq. 10 indeed very accurately describes the experimental data. From the best fit of the parameters K and b, the gamma-distribution can be evaluated, as the probability that at least one ligand interacts in a domain containing a range of binding sites comprised between x and x+dx (FIG. 5). It is clear that without BSA the domains generated in the anti-IgG SAM are very small, polydisperse and with a predominance of very small domains (centered around x~1). On the contrary, in the presence of BSA almost monodispersed giant domains are seen.

FIG. 5, in this regard, shows Gamma-distribution, $\Psi(x)$, vs. the number of binding sites, x, that best describes the experimental dose-response curves, for an anti-IgG SAM with and without BSA deposition.

List of Symbols:
    n=total number of binding sites on the whole gate. Anti-IgG in the present study
    k=number of ligands (IgG) that actually interacts with a given binding site (anti-IgG)
    N=number of ligands in the incubation volume V of a solution with a given nominal concentration c
    c=concentration of the ligands in the incubating solution, expressed in molarity M.
    $\lambda$=number of ligands per binding sites
    x=binding sites in one domain
    $\Psi(x)$=domain size distribution function As indicated in the foregoing description, the inventors have observed that in order to obtain this result, a relevant step is that of allowing an amount of BSA physisorption to the electrode after the anti-IgG chemical grafting. It is also worth noting in fact, that the quantification of the affinity ligands is possible on the anti-IgG gate that has not been treated with BSA, only in the femto molar region (data not shown), namely in a concentration range orders of magnitude higher than 60 zM and comparable to state of the art detections.

Indeed, the anti-IgG SAM, alike many other similar SAMs, is known not to cover perfectly the electrode surface even when a chemical SAM of anchoring groups are grafted directly on the gold surface 6F of the gate electrode 6. The vacancies left in the biological SAM generate spots whereat non-specific binding can occur. Adding the right amount of BSA (or other blocking agents) results in the filling of such vacancies, thereby minimizing the effect of physisorption of non-specific biomolecules (other than the affinity ligand—biomarker—to be detected) that would otherwise limit the selectivity of the biosensor response.

As demonstrated above, these features and properties were used to improve the biosensor BS sensitivity and reach few proteins detection with gate electrode 6 in a millimetric scale, thus avoiding to resort to a nanometric channel as per the prior art.

As already set forth at the beginning of the present disclosure, the inventors based their research on the observation of biological cells, such as sperm cells or eye rod cells. These cells are capable of tracking semiochemicals or photons at the physical detection limit by means of a huge number of capturing proteins or photodetectors. The bottom line in the sensing process carried out by these cells, can be summarized as follows:

single or very few target proteins or ligands (semiochemicals released by the egg cell or photons) impinge on the cell surface. This is a rather probable process as millions of receptors populate such a surface;

the receptors, such as guanylyl cyclase, present on a sperm cell rival with rhodopsin in photoreceptors (104 rhodopsins per $\mu$m2) as one of the most densely packed membrane protein.

a single or very few receptors are involved in the recognition process and eventually few receptor-ligand complexes are formed giving rise to conformational changes in very few localized sites on the sperm cells or on the rod cells surface.

As few as 2-6 recognition events over millions of highly packed receptors are involved, thereby making it impossible for the sperm cells to discriminate such a weak signal from the—so to say—"background noise" generated by the millions of receptors that did not react. This unless the isolated detection event itself generates or triggers a process that amplifies the effect.

Remarkable evidence proves that such a functional large biological interface packed with receptors is an essential prerequisite to sense environmental signals down to the physical detection limit.

In fact, a huge number of surface confined guanylyl cyclase receptors enable sperm cells to track single molecules of chemoattractants whereas olfactory neurons, by means of receptors packed on their membrane, can generate single-molecule responses while tracking few pheromones. Highly packed photoreceptors, such as those on the rod cells attached on the retina, respond to single photons, too. The effect of the patch formation in fact can involve immediately a very large fraction of the gate surface. For the rods in the retina for instance, patches as large as tens of micrometers, have been measured.

This is indeed what happens with the biological cells, as well as in the gate electrode functionalized by the method according to the invention: the change (most likely a large conformational variation) occurring when the recognition event takes place, starts from a very small area of the cell surface (functionalized gate surface 6F, which features the layer 9) and spreads to the closest receptors, thereby generating patches of receptors that are all turned into a different conformation as the signal spreads shortly following the recognition event of one single ligand.

In case of the gate electrode 6 functionalized according to the invention, the role of the BSA is actually that of making the SAM biolayer very compact and dense so as to allow the change induced by the receptor-ligand complex to spread, thereby involving a large portion of the contiguous receptors.

The structural units of the self assembled structure of specific-binding-pair-forming substance(s) are coupled mechanically and electrostatically by the BSA so that amplification of the modifications (chemical and/or structural) occurring upon a single biological recognition event is allowed and promoted.

The biases applied to the bio-functionalized gate electrode 6 either during the stabilization of the electrode before the sensing measurements or during the actual sensing process, also plays a role in generating a possible metastable state in the functionalized surface layer (i.e. in the layer applied to surface 9) that allows such spread.

This generates a change in the gate work function, which can be measured on the IDS-VGS characteristic, i.e. as the shift of the biosensor threshold voltage, that is measured as a current change. Indeed, the EG-OFET threshold voltage keep shifting towards more negative values as the gate is incubated in solutions of progressively higher concentrations of affinity ligands. This implies that a progressively larger fixed dipole moment oriented in the opposite versus as the gate field, is set in layer 9.

Importantly the theoretical model disclosed herein envisages that, in the presence of BSA, almost monodispersed giant domains form in the anti-IgG SAM as IgG affinity ligands are assayed, (FIG. 4a and FIG. 6B) while without BSA, only very small and polydisperse features can be seen (FIG. 6C). The SEM images in FIG. 4A and FIG. 6B strikingly show that indeed only on the BSA blocked anti-IgG SAM sensing IgG, wide patches are present being tens of micrometers in size and widely covered with a very dense structure of dendrites.

Figure 7A:
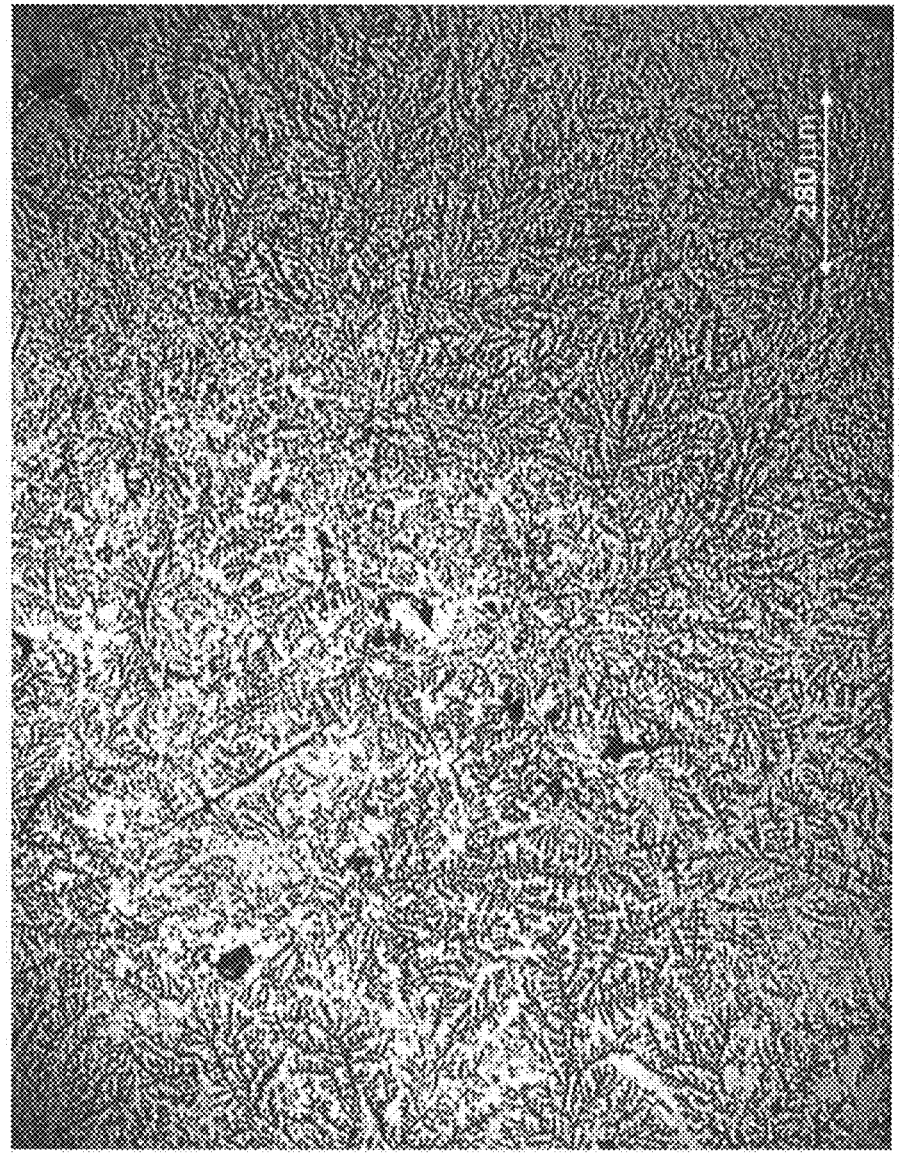
FIG. 7 shows the structures of the domains generated by the binding that are seen with an optical microscope.
Figure 7B:
Figure 7C:
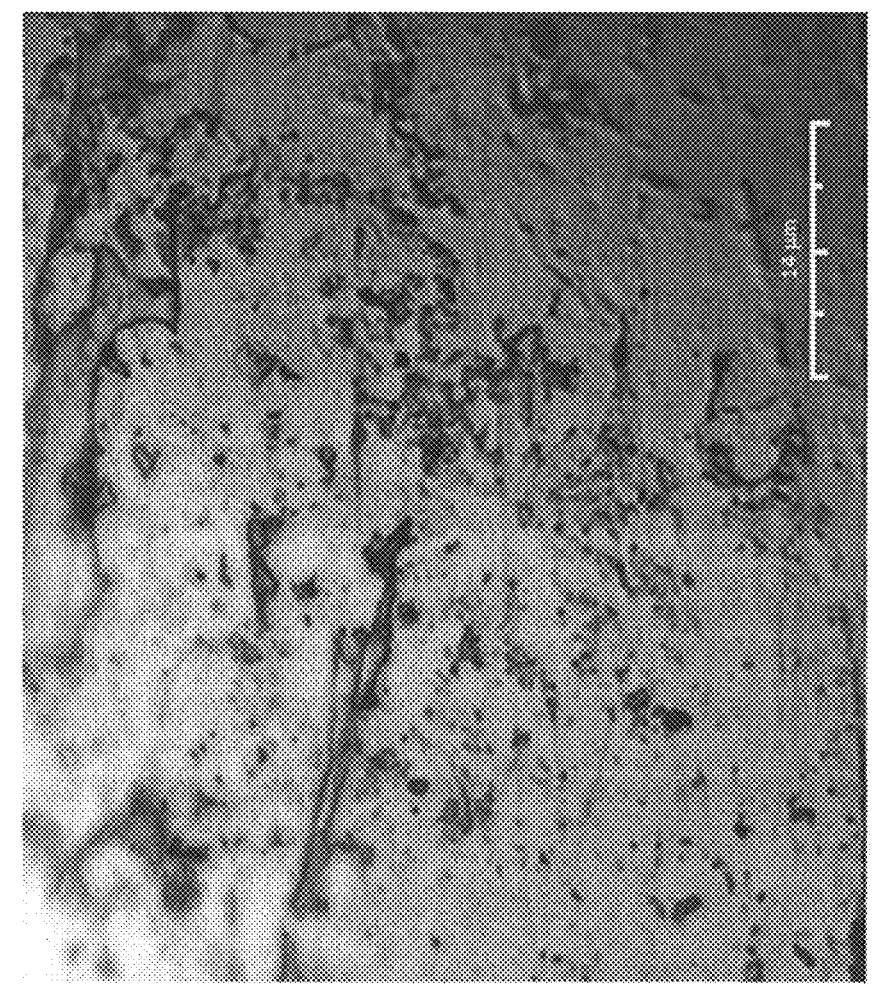

This is also evidenced by the microscope images reported in FIGS. 7A-7C. Specifically, in FIG. 7A an anti-IgG SAM on a Kapton substrate treated with ethanolamine and BSA (fully blocked) and incubated in IgG PBS solutions (6, 6×10, 6×102, 6×103, 6×104, 6×105, 6×106, 6×107 and 6×108 zM) for ten minutes each, is shown. In FIG. 7B the anti-IgG SAM on a gold platelet treated with ethanolamine and BSA (fully blocked) is used as gate to sense IgG in the whole calibration curve ranging in the 6 zM to 6 108 zM. In FIG. 7C the anti-IgG SAM on a gold platelet treated with ethanolamine is used as gate to sense IgG in the whole calibration curve ranging in the 6 zM to 6 108 zM. Two total magnification levels are provided in FIG. 7A (50×) and FIGS. 7B, 7C (1000×). The observation of dendritic structures in FIGS. 7A-7C may also open to perspective assay by simple inspection of a microscope image of the metal gate without necessarily measuring the field-induced current.

Worth to mention is that the preferred embodiment described herein and featuring an anti-IgG functionalization is taken as a model system to prove how the quantification of few antigens is feasible with a millimetric, printable EG-OFET.

As the method described herein is anyway readily applicable regardless of the specific-binding-pair-forming substance considered for functionalization of the gate electrode, such a method provides for the arrangement of plural immune-sensing systems capable to detect clinically relevant biomarkers for diseases in respect of which early diagnostic, at the physical limit, is vital (such as in tumors).

Examples—Materials and Methods

Materials: Poly(3-hexylthiophene-2,5-diyl), P3HT (Sigma-Aldrich, regioregularity >99%) with an average molecular weight of 17.5 kDa (g mol-1), was used as semiconductor with no further purification. 3-mercaptopropionic acid (3-MPA), 11-mercaptoundecanoic acid (11-MUA), 1-Ethyl-3-(3-dimethylaminopropyl)-carbodiimide (EDC) and N-hydroxysulfosuccinimide sodium salt (sulfo-NHS) for the chemical functionalization of the gold gate surface were purchased from Sigma-Aldrich and used with no further purification. The anti-human Immunoglobulin G (anti-IgG), is a Fc specific antibody affinity produced mostly in goat (molecular weight ~144 kDa) while the human IgG (~150 kDa) affinity ligand and the human IgM (~950 kDa) ligand, were extracted from human serum. Bovine Serum Albumin (BSA) has a molecular weight of 66 kDa. Both the primary and secondary antibodies as well as the BSA were purchased from Sigma-Aldrich and readily used. Water (HPLC-grade), also purchased by Sigma-Aldrich, was used with no further purification.

Electrolyte gated (EG)-OFET fabrication: Electron-beam evaporated gold source (S) and drain (D) interdigitated electrodes (50 nm, thick) were photo-lithographically defined on a Si/SiO2 substrate. A prior deposited layer of titanium (50 nm) served as adhesion layer. The distance between two differently biased fingers defines the channel length (L=5 □m), while the perimeter of all the equipotential fingers is the channel width (W=1280 μm). The transistor channel area covered by the OSC was 6.4 10-3 cm2. Prior to the electrodes patterning, the SiO2 surface was cleaned in an ultrasonic bath of solvents of increasing polarity (acetone and isopropanol respectively) for 10 min each. After the S and D electrodes definition, a P3HT solution (2.6 mg ml-1 in 1,2-dichlorobenzene) filtered with 0.2 μm filter was spin-coated at 2000 r.p.m. for 20 s and annealed at 80° C. for 1 hour. The P3HT film showed a highly hydrophobic surface characterized by a contact angle as high as 103±3°. A polydimethylsiloxane well was glued across the interdigitated channels area and was filled with 300 μL of water (HPLC grade). Alternatively, a 6 μL droplet of water was dispensed over the P3HT surface.

A gold platelet (area of 0.6 cm2 and ~2 μm thick) serving as the gate (G) electrode 6 was stably positioned on the water in correspondence of the electrodes interdigitated area as schematically depicted in FIG. 1A. The gold platelet was Bunsen burn (flame annealed) for 5 seconds and immersed in a piranha solution (H2SO4 and H2O2, 3:1 v/v) for 20 min afterwards. The platelets were also kept in boiling water for 10 min and then treated for 10 min in an ozone cleaner.

Gate bio-functionalization protocol: The chemical SAM on the gold surface was produced by depositing, at first, a layer of alkanethiols terminating with carboxylic functionalities. To this end, a 10 mM solution consisting of 10:1 ratio of 3-MPA to 11-MUA was prepared in ethanol grade, puriss. p.a. assay, >99.8%. The cleaned gold platelet was immersed in the 3-MPA and 11-MUA solution and kept in the dark under constant N2 flux for 18 h at 22° C. The strong gold-sulfur interaction results in the exposure of the carboxylic groups, activated afterwards in a 200 mM EDC and 50 mM sulfo-NHS aqueous solution for 2 h at 25° C. The anti-IgG SAM was generated, subsequently, through the anchoring of the anti-IgG antibodies to the amino groups, resulting from the chemical activation, by immerging the gate in an anti-IgG in Phosphate Buffered Saline (PBS) solution for 2 h at 25° C. The solution was composed of 0.7 μM (0.1 mg ml-1) of anti-IgG and 10 mM (KCl 2.7 mM and 137 mM NaCl) of PBS at a pH of 7.4 and an ionic strength of 162 mM. To saturate the unreacted sulpho-NHS groups, the anti-IgG SAM was treated with ethanolamine 1 M in PBS 10 mM for 1 h at 25° C. Finally, the bio-functionalized gate was immersed in a 1.5 μM (0.1 mg ml-1) BSA solution in PBS 10 mM for 1 h at 25° C. This last step is carried out to minimize the non-specific binding but also and most importantly, to drastically improve the sensitivity as discussed above. After each step of the bio-functionalization protocol, the gate was rinsed thoroughly to remove any possible residues.

Anti-IgG gate morphological characterization: The gate topography at the different functionalization steps was measured by means of a scanning electron microscope (SEM). Images of the bare gold and anti-IgG SAM were acquired with a mod. Sigma, Carl Zeiss, Oberkochen, Germany. The micrographs were obtained with the in-lens detector using an acceleration voltage of 2 kV and an aperture of 30 μm. Energy dispersive spectroscopy (EDS) was performed with a Zeiss field emission SEM (mod. Sigma) equipped with an Oxford Instruments EDS accessory (mod. INCAx-act). The spectra were collected with an accelerating voltage of 6 kV, a 9.5 mm working distance and 60 μm diameter aperture. None of the sample investigated show any surface contamination coming from salt residues coming from the PBS solution. This was expected as the surfaces were thoroughly rinsed with pure water before all the SEM investigations. Sensing measurements: The EG-OFET electronic output curves were measured by putting the gold gate electrode 6 in contact with the water in the well 11 that functions as the electrolyte gating medium. The current-voltage curve of the OFETs were measured either with an Agilent 4155C or a Keithley 4200-SCS semiconductor parameter analyzers equipped with a probe station, at room temperature. The FET were tested in the common-source configuration. As customary, for the output characteristics, the drain current (IDS) was measured as a function of the drain voltage VDS at different gate voltages VG, ranging between 0 and −0.5 V, in steps of −0.1 V. For the transfer characteristics IDS was measured as a function of VG (ranging from −0.1 to −0.7 V in steps of −0.01 V) at a constant drain voltage of −0.4 V. The voltage ranges were tuned to minimize the gate leakage current (IG) associated with ionic-electronic relay electrochemical processes involving oxidative degradation processes of the anti-IgG SAM. To minimize such processes, IG was always acquired along with IDS and all the curves were measured in the forward and reverse mode to evidence the occurrence of any hysteresis.

Before proceeding with the sensing measurements, IDS was stabilized by cycling the measurement of the transfer curve of a P3HT EG-OFET, comprising a fully cleaned bare gold platelet gate, until the last current trace reproduced exactly the three previous ones. During this process, the low-mobility trap states of the P3HT OSC are filled, leading to a stable VT value. The stable transfer curve was recorded and used as reference. A gate functionalized with a fully blocked anti-IgG SAM was then incubated (at RT and in the dark) for 10 min in 100 μL of PBS. The gate electrode 6 was removed from the PBS, washed with HPLC water, mounted on the EG-OFET (replacing the bare gold one) and a new transfer characteristic was recorded. This is addressed as the I0 current base-line. As a control experiment (carried out on a separately bio-functionalized gate) this current was measured nine times after consecutive incubation for 10 minutes in PBS of the same bio-functionalized gate. The relative changes of each trace, as compared to the first one, is as low as 1.2±0.1%.

After the measurement of the I0 base line, the same anti-IgG gate was immersed and incubated (at RT and in the dark) for 10 min in 100 μL PBS solutions of the ligands (IgG or IgM) at nominal concentrations ranging from 6 to 6.67× 108 zM. The evaluation of the error on the concentrations, or equivalently on the number of proteins sampled in 100 μL, considering both the Poisson and the dilution error, is reported in Tab. 3S. While IgG is the affinity ligand for anti-IgG, IgM, known not to selectively interact with the anti-IgG, served for negative control experiments. The incubation time was estimated to allow enough time for the IgG or IgM proteins present in the incubating solution to impinge on the anti-IgG layer. A diffusion constant as high as 4 10-11 m2 s-1 was measured for IgG in PBS incubation, resulting in a root mean square displacement explored in ten minutes of 0.4 mm. This occurrence makes it reasonable for the proteins to impinge on the gate surface during the incubation time, also considering that convective motions start when the gate is immersed in the small volume of the incubating solution. Relevant to note is also that the IgG, IgM and BSA proteins, in the given PBS solution, are negatively charged as proven by surface z-potential measurements. Specifically, IgG: z-pot=−3.4±0.2 mV; BSA: z-pot=−9.5±0.5 mV; IgM: z-pot=−2.3±0.2 mV.

After each incubation in the IgG or IgM PBS solutions, the bio-functionalized gate was washed thoroughly with the PBS solution to remove the unreacted ligands away and further I-V transfer curves were measured, taking care to positioning the gate platelet always exactly at the same height as for the measurement of the base-line, I0. The measured currents are addressed as the I signals at a given concentration. The $\Delta I/I0=[(I-I0)/I0]$ is the normalized electronic response at a given concentration and the relevant dose-response curve is obtained by plotting these data points at all investigated concentrations at the VG value that maximizes the trans-conductance $\delta IDS/\delta VG$, falling generally in the $-0.3$ V to $-0.4$ V range. One sole anti-IgG gate was used to measure the whole IgG dose curves spanning the 6 to $6.67\times108$ zM nine orders of magnitude. A second anti-IgG gate was used to measure the IgM dose curve. After measuring the whole dose curve, the bare gold gate previously used to measure the reference current level is positioned back to the EG-OFET and a final transfer curve is recorded.

The relative variation of the current measured on the bare gate, before and after the measurement of the whole dose curve, was considered acceptable only when falling within 10%. This error level was used to validate the data set and prove that the current changes measured upon exposure to the different IgG or IgM ligand concentrations, were due to the antibody-antigen interaction and not to spurious effects. To date a total of 25 whole calibration curves of IgG vs. anti-IgG have been measured along with an equal number of negative control experiments (IgM vs. anti-IgG) resulting in a total number of 225 sensing curve acquired.

Naturally, while the principle of the invention remains the same, the details of construction and the embodiments may widely vary with respect to what has been described and illustrated purely by way of example, without departing from the scope of the present invention.

The invention claimed is:

1. A method of functionalization of a gate electrode comprising the steps of:
   forming a layer of biological recognition elements on a surface of said gate electrode, wherein said layer of biological recognition elements include a self-assembled structure of one or more specific-binding-pair-forming substances, the self- assembled structure including a biological self assembled structure of one or more specific-binding-pair-forming substances,
   treating the layer of biological recognition elements with a solution containing a blocking agent to fill vacancies and prevent nonspecific binding in the self-assembled structure, wherein said blocking agent is a Bovine Serum Albumine solution,
   wherein said one or more specific-binding-pair-forming substance immobilized in said layer of biological recognition elements are packed at a density between $0.1\times10^4$ $\mu m^{-2}$ and $10\times10^4$ $\mu m^{-2}$;
   wherein the layer of biological recognition elements includes a biological self- assembled structure (B SAM) including said one or more specific-binding-pair-forming substance and a chemical self-assembled structure (C SAM) whereon said biological self-assembled structure is grafted,
   wherein each of said chemical self-assembled structure (C SAM) and biological self-assembled structure (B SAM) is a self-assembled monolayer (SAM) structure,
   wherein the chemical self-assembled monolayer (C SAM) is added to the gate electrode by means of a precursor consisting of a layer of alkanethiols terminating with carboxylic functionalities,
   wherein said treating the layer of biological recognition elements (SAM) with a solution containing a blocking agent to fill vacancies and prevent nonspecific binding in the self-assembled structure (SAM) further comprises saturation of unreacted activated carboxy groups of said chemical self-assembled monolayer (C SAM) by means of concentrated solutions of amines for a time long enough to allow the reaction with all the activated carboxylic groups.

2. The method of claim 1, wherein said one or more specific-binding-pair-forming substances include one or more of the following:
   one or more antibodies,
   anti-human Immunoglobulin (anti-hIG) antibodies,
   anti-human Immunoglobulin G (anti-IgG) antibodies,
   anti-human Immunoglobulin M (anti-IgM) antibodies,
   specific-binding-pair-forming substances for dopamine, chiral odors, DNA, PNA, human glycoprotein, inflammatory cytokines, C-reactive proteins.

3. The method of claim 1, wherein said step of treating the layer of biological recognition elements includes immerging the layer of biological recognition elements in the Bovine Serum Albumine solution in Phosphate Buffered Saline solution for a residence time comprised between 30 minutes and 2 hours, and at a temperature range of 22 to 26° C.

4. The method according to claim 1, wherein the gate electrode is further reacted in a 50 mM to 250 mM, 1-Ethyl-3-(3-dimethylaminopropyl)carbodiimide and 50 mM to 250 mM, N-Hydroxysuccinimide aqueous solution, for a residence time of 1 to 3 hours, and at a temperature of 22° C. to 26° C.

5. The method according to claim 1, wherein the biological self assembled monolayer is a self assembled monolayer of anti-human Immunoglobulin G treated with ethanolamine 1M in a Phosphate Buffered Saline solution for one hour at 25° C.

6. The method according to claim 1, wherein said biological self-assembled monolayer structure includes one or more proteins as specific-binding-pair-forming substances, wherein said one or more proteins are modified so to exhibit functional groupsreactive with the surface of the gate electrode.

7. The method of claim 1, wherein the density is between $1\times10^4$ $\mu m^{-2}$ and $2\times10^4$ $\mu m^{-2}$.

8. The method of claim 1, wherein the Bovine Serum Albumine solution comprises 0.1 mg ml-1 and the Phosphate Buffered Saline solution comprises 10 mM.

9. The method of claim 1, wherein the blocking agent is a 0.1 mg ml-1 BSA solution in Phosphate Buffered Saline (PBS) 10 mM.

* * * * *